United States Patent [19]

Allen et al.

[11] Patent Number: 5,312,729
[45] Date of Patent: May 17, 1994

[54] METHOD OF ASSAY NORMALIZED WITH NON-ANTIGEN CALIBRATOR

[75] Inventors: Gerald J. Allen, Windlesham; Madlyn D. Denyer, Loxwood; Grenville A. Robinson, Ealing, all of England

[73] Assignee: Ares-Serono Research & Development Limited Partnership, Boston, Mass.

[21] Appl. No.: 460,861

[22] PCT Filed: May 23, 1989

[86] PCT No.: PCT/GB89/00568
§ 371 Date: Mar. 6, 1990
§ 102(e) Date: Mar. 6, 1990

[87] PCT Pub. No.: WO89/11655
PCT Pub. Date: Nov. 30, 1989

[30] Foreign Application Priority Data

May 24, 1988 [GB] United Kingdom ................ 8812213

[51] Int. Cl.⁵ .................. G01N 33/53; G01N 33/537; G01N 33/543

[52] U.S. Cl. .................. 435/7.9; 435/7.92; 435/7.93; 435/7.94; 435/7.95; 435/975; 436/518; 436/815; 436/817

[58] Field of Search .............. 435/7.92, 967, 975, 435/7.93, 7.94, 7.95, 7.9; 436/518, 815, 808, 817, 530

[56] References Cited

U.S. PATENT DOCUMENTS 3,998,943 12/1976 Ullman .................. 424/12
4,299,916 11/1981 Litman et al. .................. 435/6
4,791,056 12/1988 Sizto et al. .................. 435/7

FOREIGN PATENT DOCUMENTS

0201079 12/1986 European Pat. Off.

Primary Examiner—Toni R. Scheiner
Attorney, Agent, or Firm—Ostrolenk, Faber, Gerb & Soffen

[57] ABSTRACT

The present invention relates to assay techniques for detection of ligands in solution and to means for putting such techniques into effect. In particular it relates to an improved assay technique which provides a liquid calibrator for use in standard assays in circumstances where the ligand itself is rare, expensive, or difficult to prepare in a sufficiently pure or quantifiable form.

20 Claims, 8 Drawing Sheets

METHOD OF ASSAY NORMALIZED WITH NON-ANTIGEN CALIBRATOR

BACKGROUND OF THE INVENTION

The present invention relates to assay techniques and to means for putting such techniques into effect. In particular it relates to an improved assay technique which provides a liquid calibrator for use in standard assays in circumstances where the ligand itself is unstable in solution or is rare, expensive or difficult to prepare in a sufficiently pure and/or quantifiable form.

The conventional multipoint calibration assay methodology facilitates normalisation of unknown sample values with respect to recurring variations in assay conditions. This system requires batch analysis of unknowns run with a replicate calibration or standard curve from which the unknown values are interpolated.

An improvement over this multipoint calibration assay has recently been described by Meyer and Keller in Clinical Chemistry 34 (1), 113–117 (1988) who disclose a one-point recalibration assay utilising a stored standard base curve with no end-user involvement. In practice, each individual unknown sample is assayed in parallel with a calibrator assay and the unknown value is then normalised using the ratio of the observed calibrator signal to that of the expected base curve dose. The normalised unknown sample signal is then read off the stored standard base curve and providing the calibrator, the value and the corresponding signal, for example optical density, which represents that value are selected at a point on the curve which best predicts and minimises deviations across it, due to minor variations in assay conditions, then this "single point calibration" (SPC) assay controls for variation in reagent performance while other assay conditions are controlled by the instrument.

The use of liquid calibrators in such types of assays and in kits designed for such analyses presents immediate advantages of convenience to the end-user. Unfortunately many analytes, for example prolactin, are unstable in liquid form and standard solutions may need to be reconstituted from freeze-dried preparations prior to use. Reconstitution is not only inconvenient for the end-user but, more importantly, introduces considerable room for imprecision which makes the use of freeze-dried standards, particularly with the single point calibration assay described above, potentially inaccurate and thus of very limited use. Thus, the present invention provides a method of assay which incorporates the use of an alternative calibrator which is stable as a liquid preparation.

SUMMARY OF THE INVENTION

In its broadest aspect the invention thus provides a method of assay for a ligand in a sample comprising
i) incubating the sample, sequentially or simultaneously, with a first specific binding partner to the ligand and with an aliquot of reagent X comprising a second specific binding partner to said ligand or a ligand analogue, said reagent X being bound, directly or indirectly, to a detectable label;
ii) removing substantially all of said first specific binding partner and an amount of said reagent X from the assay medium, the amount of reagent X removed being a function of the amount of said ligand; and
iii) determining, by means of said detectable label, the amount of reagent X removed from the assay medium;

characterised in that the assay is normalised by comparison with a standard assay which includes the step of incubating an aliquot of the said reagent X or an aliquot of a reagent Z (reagent Z comprising an appropriate reagent labelled analogously to reagent X) with a specific binding partner (not being said ligand) therefor.

Conventional standard assays utilize standard solutions containing known amounts of the ligand under assay. However, the standard assay according to the present invention utilises a non-ligand calibrator.

DESCRIPTION OF THE PREFERRED EMBODIMENTS

In one embodiment (hereinafter "embodiment (A)") of the present invention the standard assay may be carried out by
iv) incubating an aliquot of reagent X as defined above with a standard solution of a calibrator reagent Y which comprises a specific binding partner to said reagent X;
v) removing substantially all of said calibrator reagent Y and an amount of said reagent X from the assay medium in the same manner as that used to remove the first specific binding partner in step (ii), the amount of reagent X removed being directly proportional to the amount of said calibrator reagent Y; and
vi) determining the amount of reagent X removed from the assay medium as in step (iii).

In embodiment (A), the specific binding partner for reagent X is provided by reagent Y.

In an alternative embodiment (hereinafter "embodiment (B)") the standard assay may be carried out using a standard solution of a calibrator reagent Z in place of both the first specific binding partner and reagent X used in the sample assays. Thus, for example, in a typical sandwich assay for an antigen where reagent X comprises a detectably labelled antiantigen antibody and the first specific binding partner comprises a hapten-labelled anti-antigen antibody, calibrator reagent Z may comprise an equivalently hapten-labelled and detectably labelled entity. Preferably calibrator reagent Z simply comprises reagent X additionally labelled with the hapten used to label the first specific binding partner employed in the sample assays In such an embodiment, the specific binding partner for reagent Z may comprise an antihapten antibody conjugated to solid phase It is to be understood that when reagent X comprises a second specific binding partner to the ligand, said ligand must carry two or more epitopic sites, which may be the same or different Where the ligand carries two or more identical epitopic sites it will be appreciated by those skilled in the art that the second specific binding partner may be the same as the first specific binding partner.

The term "ligand analogue" as used herein refers to a species capable of complexing with the same binding site of the same specific binding partner as the ligand under assay, and includes inter alia within its scope a known quantity of the ligand under assay.

It will be recognised that when reagent X comprises a second specific binding partner to the ligand a "sandwich-type" assay will result, in the presence of ligand, in complex formation between the first and second specific binding partners, indirectly via the ligand, such that the amount of reagent X bound will be directly proportional to the amount of ligand present in the sample. In a sandwich-type assay it is clear that the quantities of said reagent X and said first specific binding partner will, in order to obtain binding of reagent X in amounts proportional to the amount of ligand under assay, be present in an excess amount compared to the quantity of ligand in the sample.

Alternatively, when reagent X comprises a ligand analogue a "competition-type" assay results and a complex is formed directly such that the amount of reagent X bound will be inversely proportional to the amount of ligand present in the sample.

In both sandwich and competition assays suitable sample dilutions may be required in order to quantify the amount of ligand present in the sample In embodiment (A) it is particularly preferred to use the same quantities of reagent X in both the sample assay(s) and the standard assay(s).

Suitable detectable labels for reagent X include those conventionally used in immunoassays such as radioactive isotopes, fluorophors and enzymes.

Removal of the first specific binding partner from the medium may be carried out by any suitable means already known in the art. Thus, for example, the first specific binding partner may be removed by means of a solid phase carrying a specific binding partner to said first specific binding partner. Conveniently the solid phase may be particles, beads, wall coatings on the reaction vessel or inserts. Analogous methods may be used for removal of reagents Y and Z in embodiments (A) and (B) respectively.

The term "normalising" as used herein refers to the comparison of the observed reading obtained from an assay of a sample containing an unknown quantity of ligand with the observed reading obtained from a standard calibrator assay. The reading obtained from a known quantity of the calibrator reagent Y or Z, which unlike conventional standards is not simply a known amount of the ligand under assay, is itself standardised by comparison with a stored standard base curve derived from a single series of assays carried out using various known amounts of the ligand i.e. a conventional multipoint calibration curve. Thus, the reading obtained from the assay of a known amount of the calibrator reagent Y or Z is proportional to the readings obtained from a known amount of the ligand under assay and hence can be used to normalise the unknown sample readings The use of a single calibration assay is usually preferred for reasons of simplicity and economy. However, it will be understood that under certain conditions or with certain assay systems the use of a further normalisation may be preferred, for example using a series of varying amounts of calibrator reagent Y or Z to provide a multipoint calibration curve.

It is clear that, in order to fall within the scope of the invention, the calibrator reagent Y must satisfy the following four criteria:

1) It must specifically bind to labelled reagent X;
2) It must be removed from the assay medium in a manner similar to that of the first specific binding partner;
3) It should mimic the readings observed relative to a standard curve in a predictable and reliable manner and hence can be calibrated to ligand amount on the standard curve; and
4) It must be stable in solution at working concentrations and temperatures.

Calibrator reagent Z used in embodiment (B), which itself incorporates detectable label, must satisfy points 2–4 above.

The use of the non-ligand calibrator reagent Y or Z as defined herein in the method of assay according to the present invention is of great advantage where the ligand itself is unstable in solution or is rare or difficult and/or expensive to obtain in a sufficiently pure form for the preparation and prolonged storage of numerous conventional standard solutions. Standards which are unstable in solution are, at present, often prepared as a more stable freeze-dried product but the necessary reconstitution procedure then carries the disadvantages of inconvenience to the end-user and imprecision incurred by adding a specified volume of solution to the standard before use.

According to another aspect of the invention there is provided a kit for carrying out a method of assay as described herein which comprises a reagent X as defined above, a first specific binding partner to the ligand under assay and a standard solution of calibrator reagent Y or Z as defined above.

Kits according to the invention may if desired additionally contain a reagent comprising a solid phase carrying a binding partner to reagent Y or Z respectively.

A preferred embodiment (A) of the invention will be particularly described hereinafter with reference to an antigen as the ligand and where the first specific binding partner comprises an antibody to the said antigen. However, the invention is not to be taken as limited to assays of antibodies or antigens. Examples of ligands which may be assayed by the method of the invention are given in Table 1 below, together with an indication of a suitable specific binding partner in each instance.

TABLE 1

| Ligand | Specific Binding Partner |
|---|---|
| antigen | specific antibody |
| antibody | antigen |
| hormone | hormone receptor |
| hormone receptor | hormone |
| polynucleotide strand | complementary polynucleotide strand |

TABLE 1-continued

| Ligand | Specific Binding Partner |
| --- | --- |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinising hormone (LH), human chorionic gonadotrophin (hCG), follicle stimulating hormone (FSH), insulin and prolactin) or non-peptide hormones, (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, viruses such as Influenza, parainfluenze, adeno-, hepatitis, respiratory and AIDS viruses, or microorganisms.

It will be understood that the term "antibody" used herein includes within its scope:

(a) any of the various classes or sub-classes of immunoglobulin, e.q. IgG, IgA, IgM, or IgE derived from any of the animals conventionally used, e.g. sheep, rabbits, goats or mice, (b) monoclonal antibodies, (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacterial fragments, cells, cell fragments and viruses) and haptens which may be rendered antigenic under suitable conditions.

Thus, in one embodiment of the invention the ligand is a hapten or a multiple epitope antigen such as prolactin and the first specific binding partner is an antibody, which may be polyclonal or monoclonal. The first specific binding partner may be effectively removed from the assay mixture by means of a solid phase carrying a specific binding partner to the said first specific binding partner. Thus, for example, the solid phase may carry an antispecies antibody directed against the species in which the first specific binding partner was raised. Alternatively, where the first specific binding partner is labelled with a hapten such as FITC, the solid phase may carry an antibody directed against said hapten analogous to the technique described in EP-0105714.

In a sandwich-type assay according to the present invention, for example where reagent X comprises an antibody against the antigen to be assayed, the calibrator reagent Y may comprise a known amount of an anti-species antibody directed against the species in which the reagent X antibody was raised.

Alternatively, in a competition-type assay according to the invention, for example where reagent X comprises an analogue of the antigen under assay, the calibrator reagent Y may comprise a known amount of the said first specific binding partner antibody.

It will be appreciated that the method according to the invention will be particularly advantageous in the case of sandwich-type assays because a single type of calibrator reagent Y could be utilised in any number of different assay kits for different ligands providing the reagent X antibody had been raised in the same species and providing identically hapten-labelled e.g. FITC-labelled first specific binding partners were used.

The method and kit according to the invention are suitable for use in conjunction with many different types of assay apparatus including, inter alia, devices for optical immunoassay, for example such as are described in EP-A-171148, or optical structures which are capable of exhibiting surface plasmon resonance, for example such as are disclosed in EP-A-112721.

Figure 1:
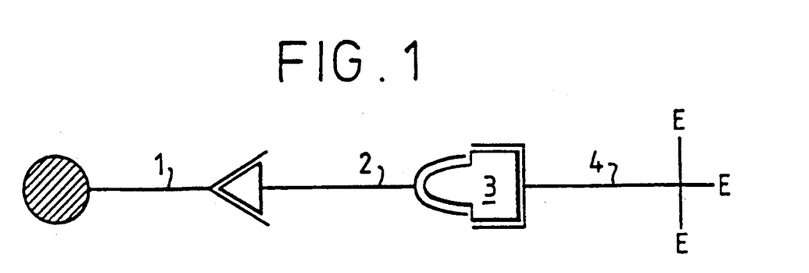
FIG. 1 illustrates an immunocomplex formed in a conventional sandwich assay.
Figure 2:
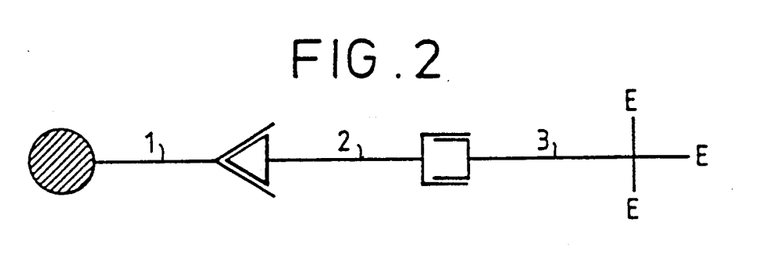
FIG. 2 illustrates an immunocomplex formed in accordance with embodiment (A) of the present invention.
Figure 6:
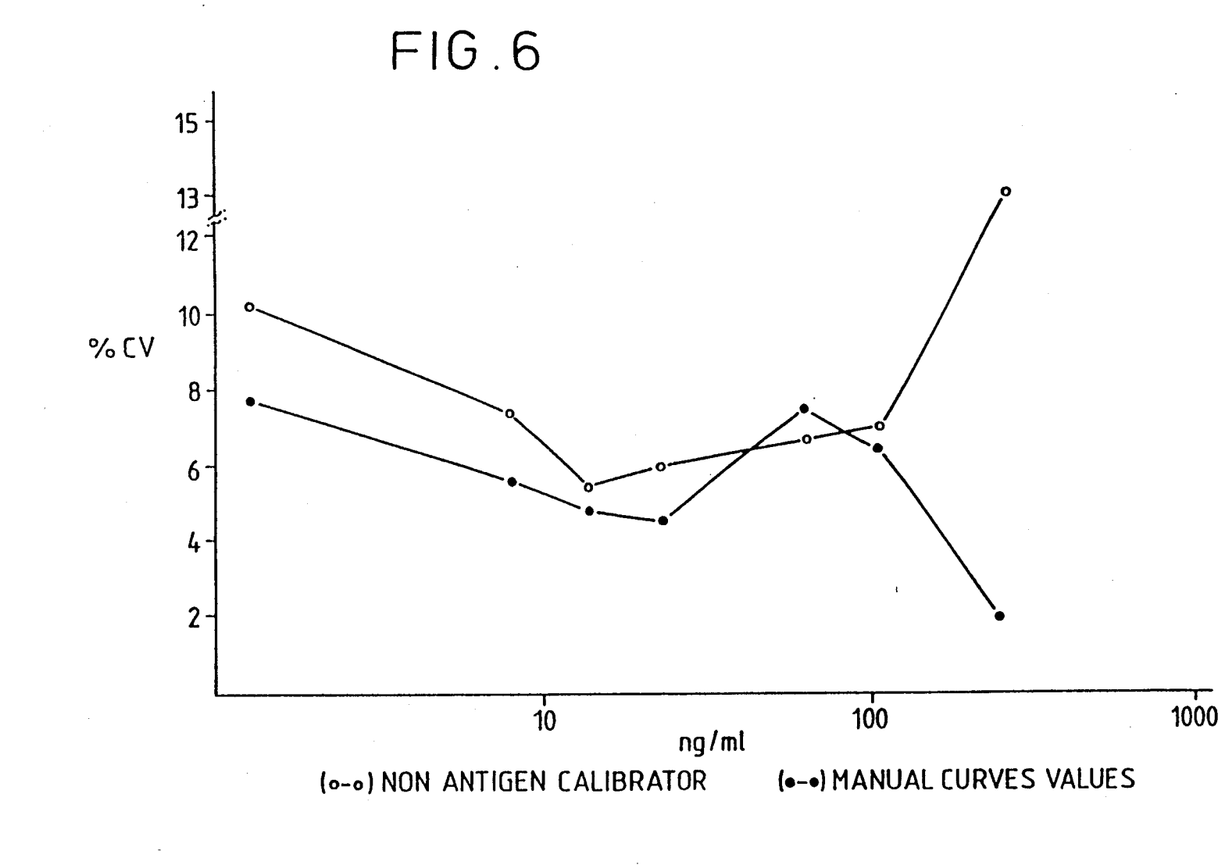
FIG. 6 illustrates a precision profile of sample values obtained using non-antigen calibrator compared to conventional standard curve derived values.
Figure 7:
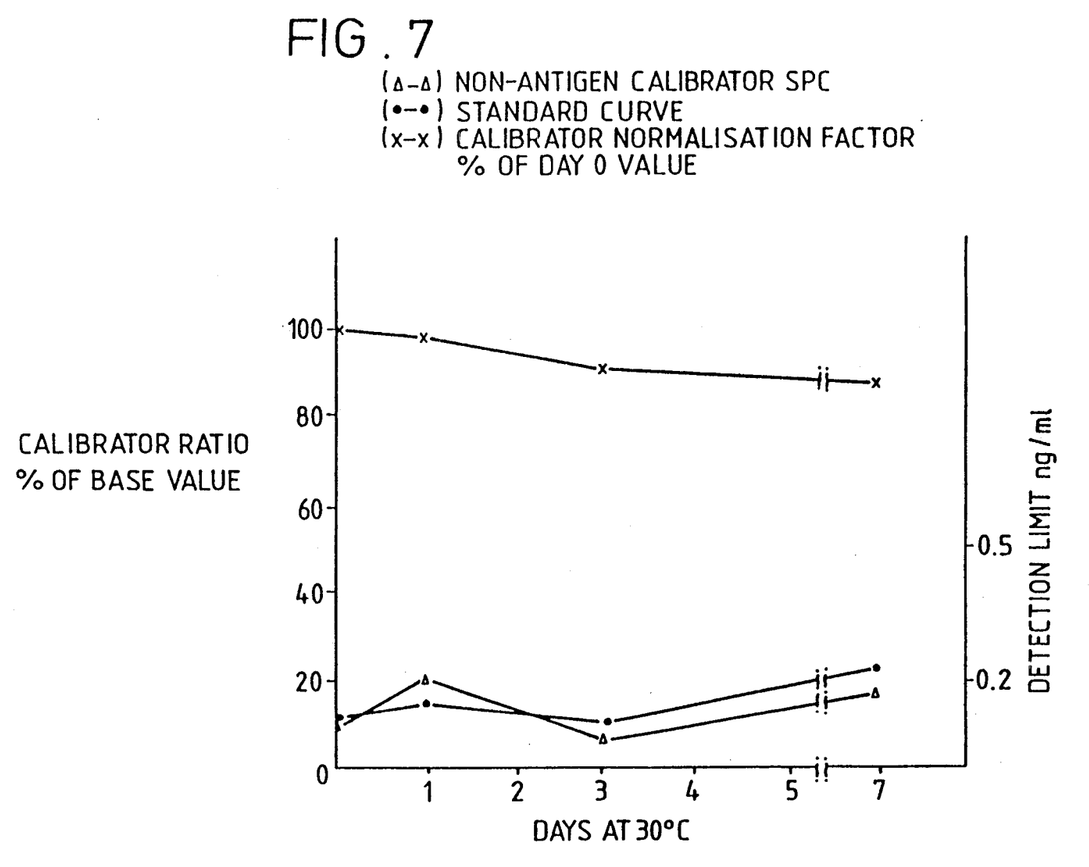
FIG. 7 illustrates the effect of ageing of reagents on detection limits using non-antigen calibrator compared to standard curve derived values.
Figure 8:
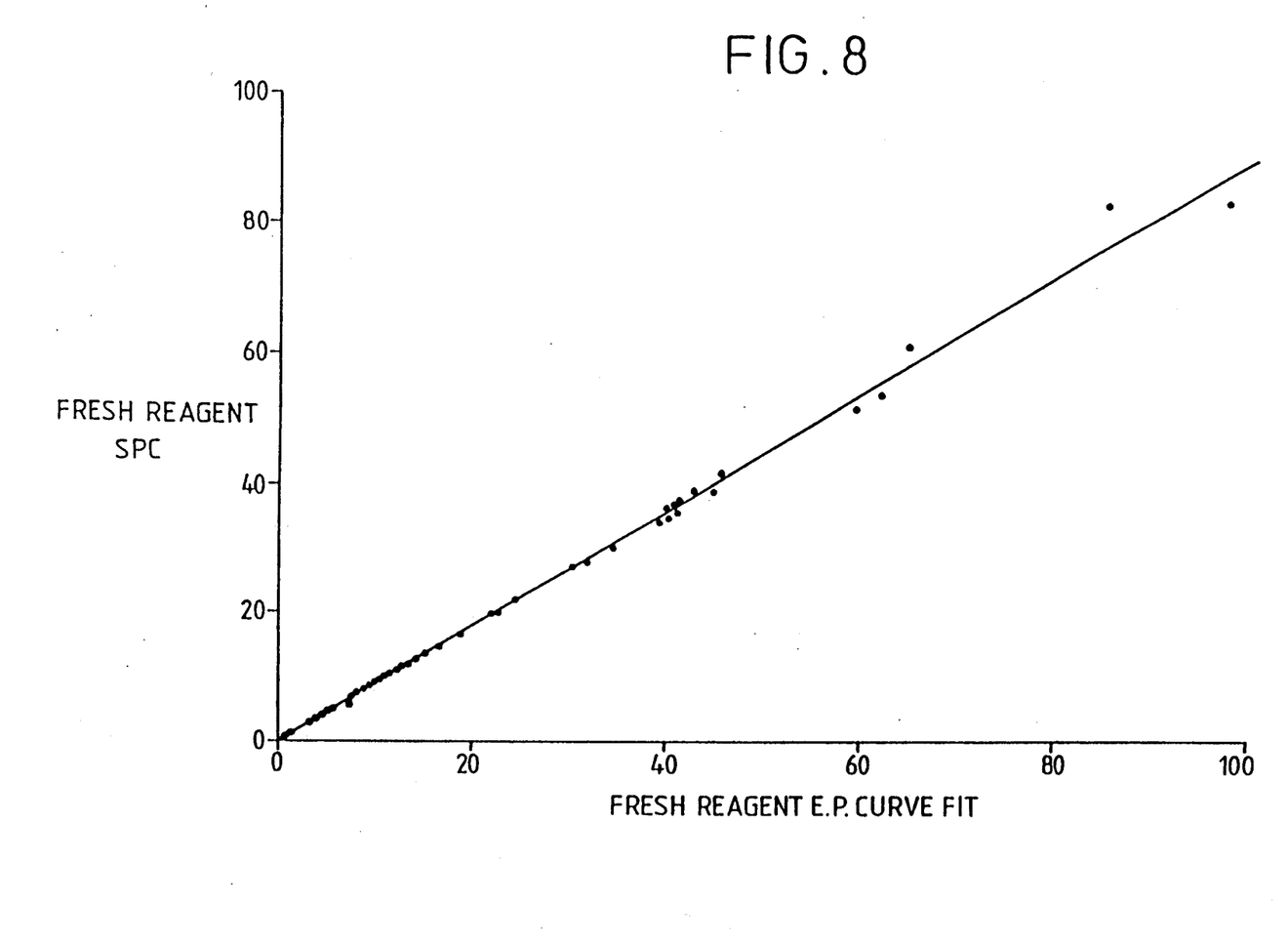
FIGS. 8 and 9 illustrate prolactin correlation curves using fresh and aged reagents respectively.
Figure 9:
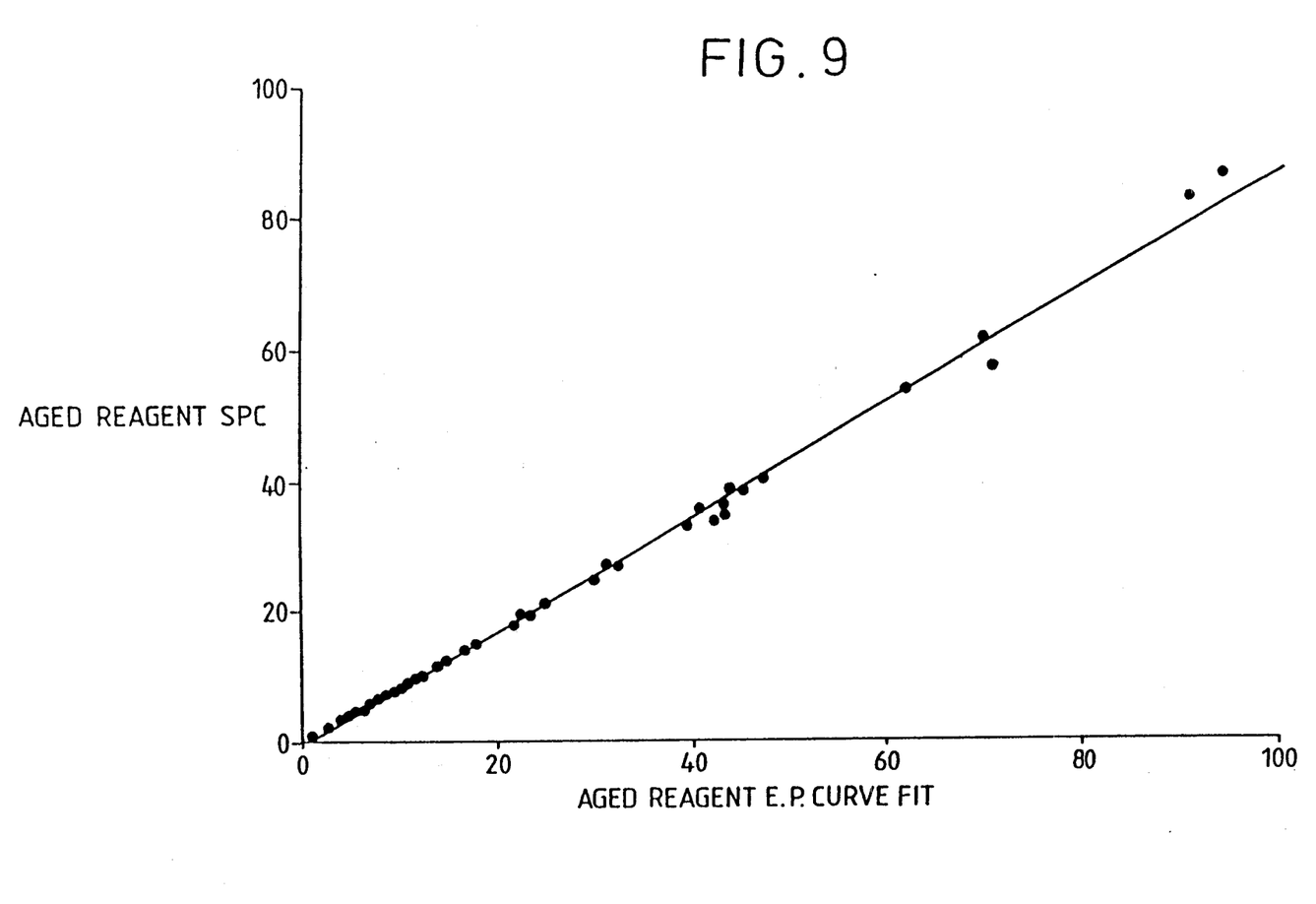
Figure 10:
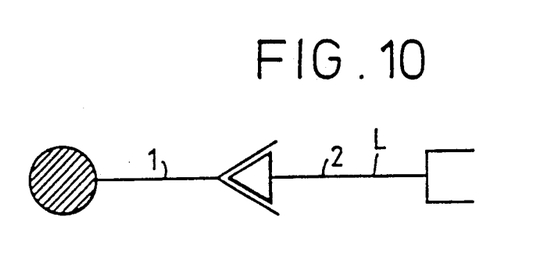
FIG. 10 illustrates an immunocomplex formed in accordance with embodiment (B) of the present invention.

For a better understanding of the present invention reference is made to the accompanying drawings wherein: FIG. 1 shows schematically a conventional sandwich type immunocomplex wherein:

1 = solid phase sheep anti-FITC polyclonal antibody
2 = FITC-labelled mouse anti-hPrl monoclonal antibody
3 = prolactin (hPrl) antigen
4 = enzyme-labelled mouse anti-hPrl monoclonal antibody;

FIG. 2 shows schematically a sandwich-type immunocomplex according to an embodiment of embodiment (A) of the present invention wherein:

1 = solid phase sheep anti-FITC polyclonal antibody
2 = FITC-labelled sheep anti-mouse polyclonal antibody
3 = enzyme-labelled mouse anti-hPrl monoclonal antibody;

FIGS. 3 to 7 are curves referred to in the Example; FIGS. 8 and 9 show the prolactin correlation curves for fresh and aged reagent respectively; and FIG. 10 shows schematically a complex formed according to embodiment (B) in which 1 = anti-FITC solid phase
2 = FITC-labelled antibody also carrying detectable label L.

In a conventional standard sandwich assay for, for example prolactin, the calibrator is a known amount of the ligand under assay (prolactin) which acts as a linker or bridge between the solid phase for separation and the tracer reagent for signal generation, for example as shown schematically in FIG. 1.

However, in the embodiment of the invention exemplified hereinafter and shown schematically in FIG. 2 an FITC-labelled sheep anti-mouse polyclonal antibody was used as calibrator reagent Y to form the bridging component between the sheep anti-FITC solid phase separation system and the enzyme-labelled signal generating mouse monoclonal antibody.

Prolactin is notoriously unstable stored in liquid state at 4° C., which is the requirement for ready-to-use calibrators and until now all known manufacturers of prolactin immunoassay kits offered no alternative to using freeze-dried preparations of the hormone. Stability over the reagent shelf-life of approximately nine months is assured with the freeze-dried product, but this carries the disadvantages described above and thus the advantages of the method of assay according to the present invention are self-evident.

The following non-limiting Example illustrates a method of assay carried out in accordance with the invention.

EXAMPLE 1

Liquid non-antigen calibrator used in Single Point Calibration of the Prolactin Immunoenzymetric Assay (IEMA)

Preparation of Starting Materials

1. Preparation of anti-prolactin monoclonal antibodies

Monoclonal antibodies were obtained from mouse ascites fluid by the process reported by Milstein and Kohler in Nature 256 (1975) 495–497.

Antibodies from individual hybridoma cell lines were screened to identify those producing antibody to discrete antigenic determinants. Those having the highest affinities to prolactin were selected for use in the assay.

2. Preparation of alkaline phosohatase/anti-prolactin conjugate 0.16 ml N-succinimidyl 4-(N-maleimidomethyl) cyclohexane-1-carboxylate (SMCC) (60 mM in dimethylformamide-DMF) was added to 1.6 ml of alkaline phosphatase (2 mg/ml in 50 mM sodium borate, 1 mM magnesium chloride, 0.1 mM zinc chloride, pH 7.6) and incubated for 1 hour at 30° C. The enzyme was separated by passage through a Sephadex G-25 medium column (1×35 cm) equilibrated in 0.1 M Tris, 1 mM magnesium chloride and 0.1 mM zinc chloride, pH 7.0. The purified enzyme was stored at +4° C. until required.

16.3 µl of N-succinimidyl 3-(2-pyridyldithio) propionate (SPDP) (25 mM in ethanol) were added to 1 ml anti-Prolactin monoclonal antibody (3 mg/ml in 200 mM sodium propionate, pH 6.0) and incubated for 30 minutes at room temperature. The antibody was separated by passage through a disposable Sephadex -25 column (PD-10) equilibrated in 200 mM sodium acetate buffer, pH 4.5. Dithiothreitol (1 M) was added to the antibody (1/20 of antibody volume added) and left for 10 minutes at room temperature. The antibody was desalted using a Sephadex G-25 medium column (1×35 cm) equilibrated in 200 mM sodium propionate, pH 6.0.

Antibody and alkaline phosphatase prepared as above were mixed in an equimolar ratio and left to conjugate for 24 hours at 4° C. The resulting conjugate was purified by high performance liquid chromatography (HPLC) on a TSK 3000 SW column equilibrated in 200 mM sodium propionate, 1 mM magnesium chloride and 0.1 mM zinc chloride at pH 6.0. The conjugate was diluted in assay buffer to a concentration of 2.5 µg/ml for use in the assay.

3. Preparation of anti-prolactin monoclonal antibody conjugated to fluorescein isothiocyanate (FITC)

2.5 mg of anti-prolactin antibody, specific for a different epitope on the prolactin molecule than the antibody conjugated to alkaline phosphatase, was dissolved in bicarbonate buffer (0.02 M, pH 9.1) and mixed with 500 µl of 0.5 mg/ml FITC.

After an 18 hour incubation at 4° C., conjugate was purified by passage down a Dephadex G-25 column equlibrated with sodium propionate buffer (0.2 M, pH 6.0).

4. Preparation of sheep anti-mouse antibody conjugated to fluorescein isothiocyanage (FITC)

The anti-mouse antibody was a conventional polyclonal antiserum obtained by immunising sheep with purified mouse IgG. The antisera obtained was then purified twice by salt precipitation using 18% w/v sodium sulphate; after which it was finally purified by passage down a TSK 3000 SW silica-base HPLC column equilibrated with 0.2 M sodium propionate buffer pH 6.0. The antibody pool was then dialysed into 0.2 M sodium bicarbonate buffer pH 9.0. The purified antimouse product was then conjugated to FITC as described above.

5. Preparation of anti-FITC antibody covalently coupled to magnetisable solid phase The anti-FITC antibody was a conventional polyclonal antiserum obtained by immunising sheep with FITC conjugated to keyhole limpet haemocyanin. The magnetisable cellulose particles were a composite of cellulose containing approximately 50% black ferric-(ous) oxide ($Fe_3O_4$), with mean particle diameter of 3 microns (see Forrest and Rattle, "Magnetic Particle Radioimmunoassay" in Immunoassays for Clinical Chemistry, p, 147–162, Ed. Hunter and Corrie, Churchill Livingstone, Edinburgh (1983)). Anti-FITC antiserum was covalently coupled to the magnetisable cellulose following cyanogen bromide activation of the cellulose according to the procedure of Axen et al., Nature 214, 1302–1304 (1967). The antiserum was coupled at a ratio of 2 ml antiserum to 1 gram of magnetisable solid phase.

The solid phase was diluted to 6.0 mg/ml in 50 mM Tris/HCl buffer, pH 8.0, containing 0.1% sodium azide, 0.5% bovine serum albumin (BSA), fraction V, 0.25% Tween 20 and 0.5% methocell.

6. Preparation of prolactin standard solutions

A preparation of freeze-dried prolactin, calibrated against International Reference Preparation 75/504, was diluted in heat inactivated bovine serum to give concentrations of 0, 2.09, 5.24, 9.95, 25.53, 99.05, 247.3 ng/ml (1.0 ng/ml=20 µU/ml).

7. Preparation of the assay buffer

The assay buffer consisted of 05.% BSA, fraction V, 0.2% sheep serum, 1 mM magnesium chloride, 0.1 mM zinc chloride, 0.1 M sodium chloride and 0.2% sodium azide in 0.1 M Tris/HCl, pH 8.0.

8. Preparation of the wash buffer

The wash buffer consisted of 0.9% sodium chloride in 0.01 M Tris/HCl, pH 8.6.

9. Preparation of the substrate buffer

The substrate buffer consisted of 1.1 M solution of diethanolamine, 0.9% sodium chloride and 1 mM magnesium chloride at pH 8.6. This buffer then had the substrate for alkaline phosphatase (3.0 mM phenolphthalein monophosphate) dissolved in it.

10. Preparation of the stop solution

The stop solution was prepared by adjusting a solution comprising 100 mM sodium carbonate, 50 mM CAPS (3-[Cyclohexylamino]-1-propanesulfonic acid) to pH 13.4 by adding 240 mM NaOH.

Assay Methodology

100 µl aliquots of each standard, calibrator or unknown sample were pipetted in duplicate into polystyrene assay tubes. 100 µl of each of the appropriate antibody conjugates were added to each tube. All tubes were mixed and incubated for 15 minutes at 37° C.

200 μl magnetisable anti-FITC solid phase were then added to each tube followed by mixing and incubation for 5 minutes at 37° C.

After magnetic separation of the solid phase the supernatant was decanted and 500 μl wash buffer added to all tubes. The tubes were mixed and again magnetically separated and the supernatant decanted off. This wash procedure was repeated two more times.

300 μl of substrate solution were added to all tubes, which were then mixed and incubated for 10 minutes at 37° C.

1.0 ml stop solution was added to all tubes following which the assay was magnetically separated.

The absorbances of the supernatant were determined at 550 nm and 492 nm on the Ocean Scientific Chemstat Spectrophotometer. The use of the dual wavelength is applicable as cited in EP-249357.

Experiments to select and calibrate the non-antigen calibrator

The optimum calibrator value was assessed with respect to both accuracy and precision of sample measurement across the standard curve as derived by single point calibration (SPC) using reconstituted freeze-dried calibrator. Ten standard curves and controls were run. A base curve was set up by combining the 10 curves. This base curve, fitted by the 5 parameter logistic fitting programme, is defined by the 5 parameters generated by the fitting procedure. The base curve was then used in conjunction with the formulae described in CP-0190006 to define the suitable calibrator.

The calibrator value selected from the range tested (each standard was used in turn as calibrator plus other intermediate antigen values) was that giving the best compromise between precision and accuracy.

Figure 3:
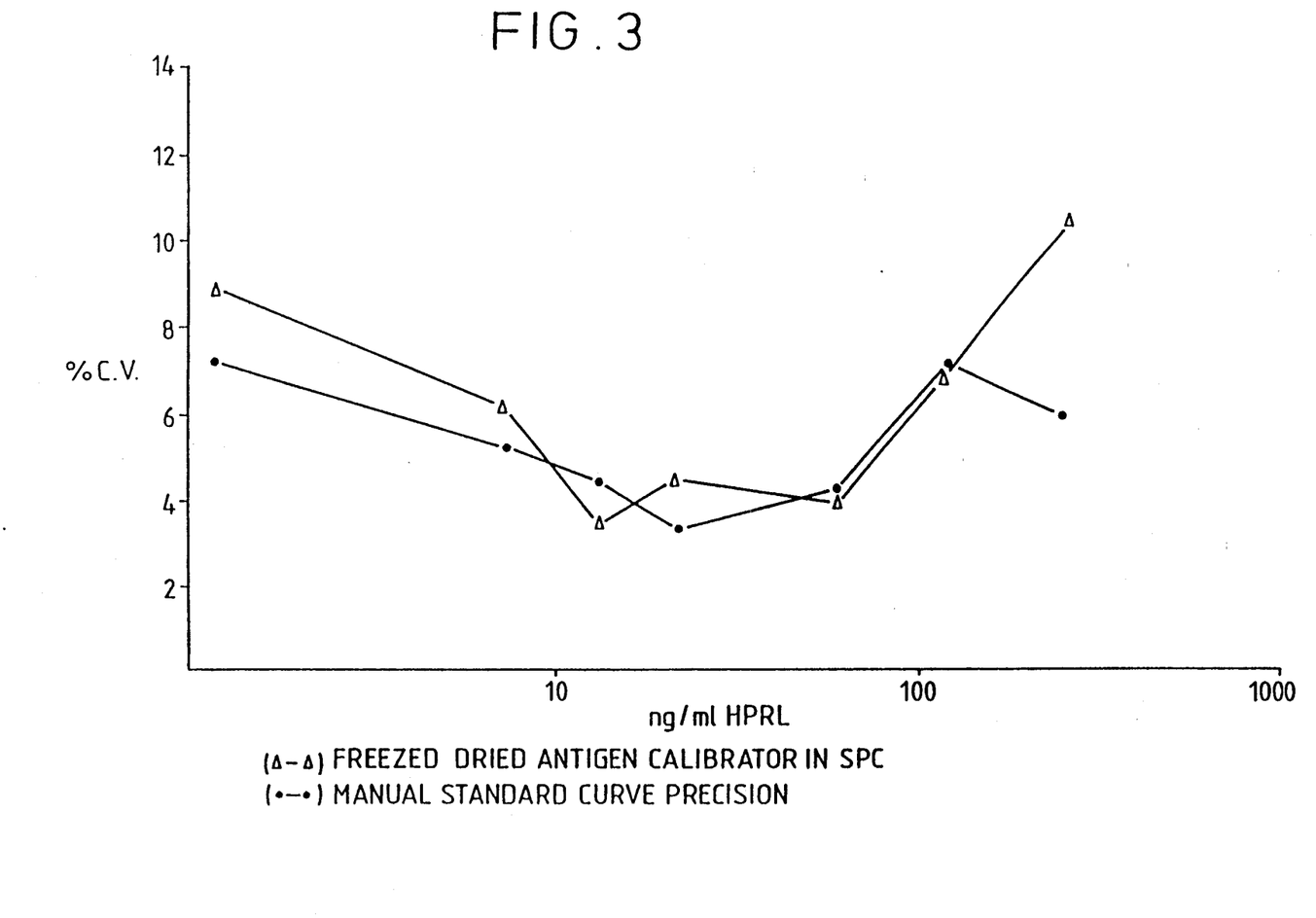
FIG. 3 illustrates a precision profile of sample values obtained using antigen calibrator compared to conventional standard curve derived values.

FIG. 3 demonstrates the precision profile of SPC unknown sample values obtained using the selected freeze-dried calibrator with SPC to normalise the unknown sample signals which are then read off the base curve, compared to the precision obtained for the same samples with values read from conventional standard curves. Each sample was assessed by both procedures in ten separate assays.

Figure 4A:
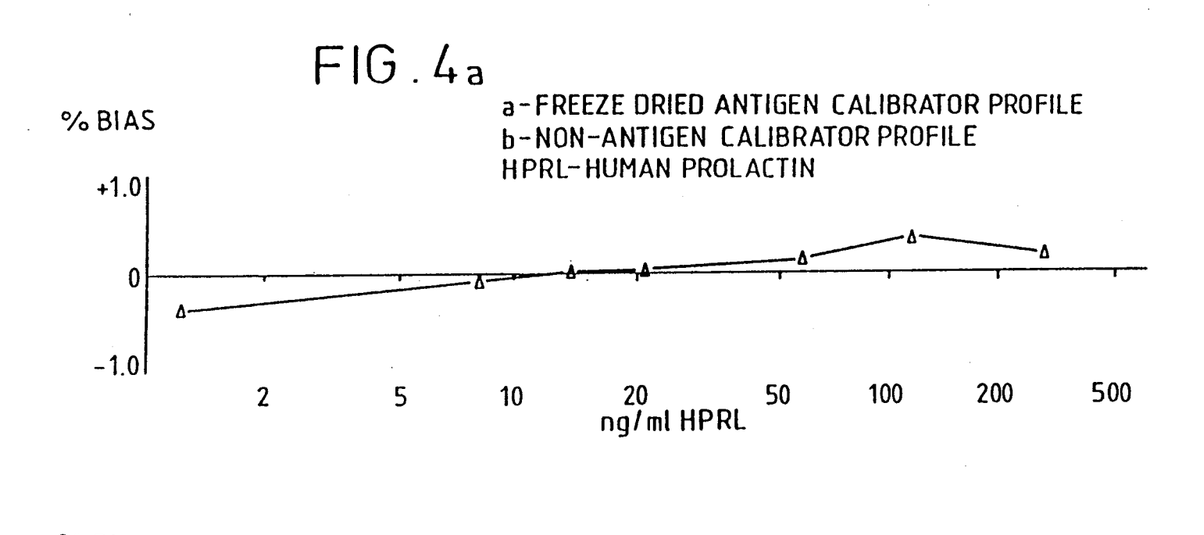
FIGS. 4a and 4b illustrate bias profiles of antigen calibrator (4a) compared to non-antigen calibrator (4b).

FIG. 4a on the other hand demonstrates the mean SPC% bias observed over the range. Bias was calculated thus:

$$\frac{\text{Reference value} - SPC \text{ value}}{\text{Reference value}} \times 100$$

Figure 5A:
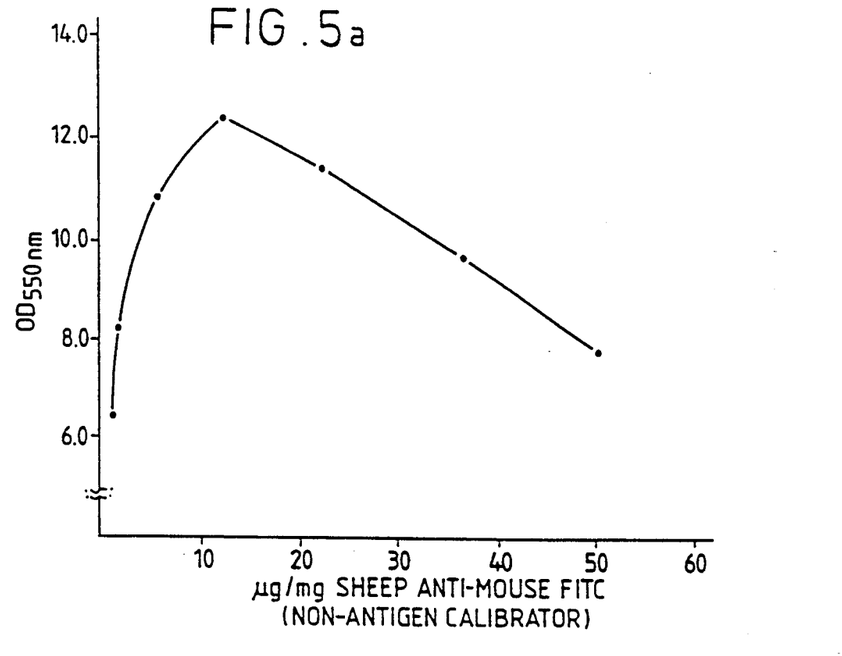
FIGS. 5a and 5b illustrate titration curves of the non-antigen calibrator.
Figure 5B:
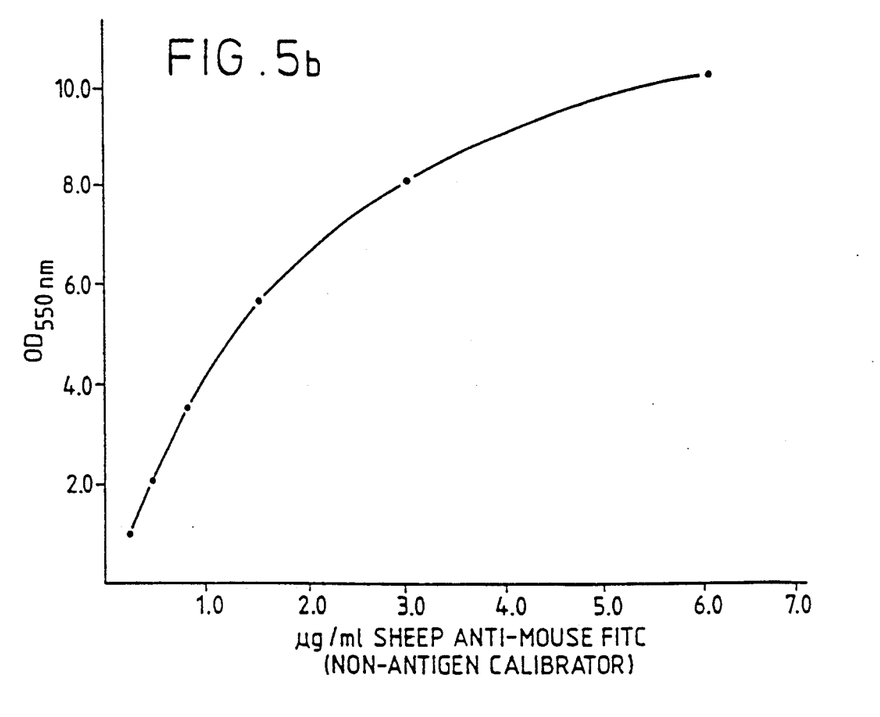

Reference values were obtained from the base curve derived values. Having selected the value of the antigen calibrator, the non-antigen calibrator was titrated by dilution in assay buffer (see FIG. 5). Various concentrations of the non-antigen calibrator were run in the assay and the concentration giving an OD similar to that of the selected antigen was chosen and calibrated (i.e. run as unknown with standard curves). Its corresponding antigen value was interpolated from the standard curve. In this way the equivalent antigen value was assigned to the non-antigen calibrator such that:

Antigen calibrator concentration (ng/ml or μU/ml) with x OD units = y OD units non-antigen calibrator with equivalent antigen value (ng/ml or μU/ml).

The non-antigen calibrator—sheep anti-mouse FITC—concentration of 1.2 μg/ml gave an OD 550 nm of 5.34 and had an equivalent antigen value read from the standard curve of 82.44 ng/ml.

Experiments to demonstrate performance of non-antigen calibrator

Figure 4B:
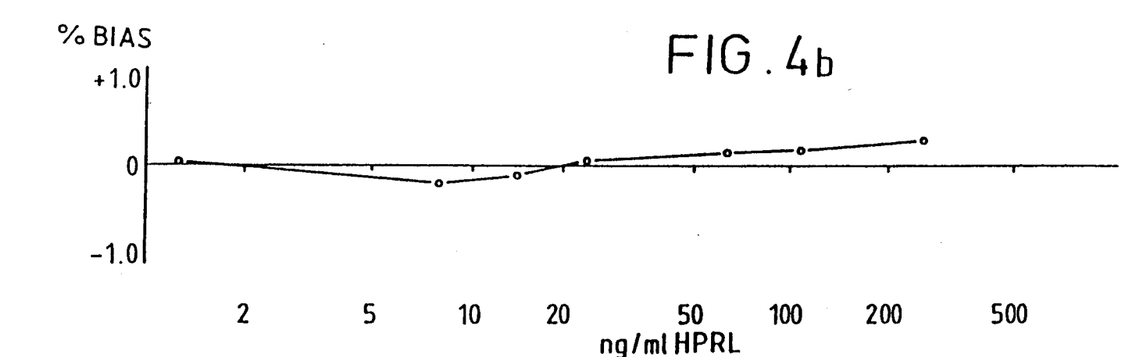

Having established the non-antigen calibrator value in ng/ml and OD, the single point calibration procedure was performed as for the freeze-dried calibrator. FIG. 6 demonstrates the precision profile of SPC unknown sample values obtained using the non-antigen calibration which normalises the unknown signals which are then read off the base curve vs standard curve derived precision profile. Each sample was again assessed by both procedures in ten separate assays. FIG. 4b shows the mean % bias observed when SPC was applied with the non-antigen calibrator.

The non-antigen calibrator's performance was demonstrated to be equivalent to that of the freeze-dried antigen calibrator in these experiments.

Experiments to demonstrate non-antigen calibrator performance vs Standard Curve

A clinical validation

Sensitivity

Detection limit for standard curves was assessed as means (x) of 10 replicates of zero run with each standard curve +2 standard deviations (2SD). This value x+2SD was read off the standard curve.

The detection limit by SPC was determined by two methods:

1) The x+2SD OD of 10 replicates of zero obtained for the standard curve was normalised on SPC using the calibrator. This normalised OD signal was then read off the base curve.

2) Alternate zero and calibrator was run in the assay. Each calibrator signal was used to normalise its pair zero. The mean of the normalized values was then read off the base curve giving the SPC detection limit.

Table 2 below shows the effect of SPC on detection limit.

TABLE 2

| | SPC Detection Limit | |
|---|---|---|
| Zero Signal | Calibration Ratio | Normalised Signal |
| 0.069 | 1.027 | 0.071 |
| 0.064 | 1.021 | 0.065 |
| 0.062 | 0.985 | 0.061 |
| 0.064 | 0.921 | 0.059 |
| 0.058 | 0.971 | 0.056 |
| 0.058 | 0.973 | 0.056 |
| 0.065 | 0.959 | 0.062 |
| 0.068 | 0.981 | 0.067 |
| 0.062 | 0.943 | 0.058 |
| 0.062 | 0.959 | 0.059 |
| x = 0.0632 | x = 0.9695 | x = 0.0614 |
| SD = 0.0036 | SD = 0.036 | SD = 0.0049 |
| Detection Limit = 0.046 ng/ml | % CV = 3.2 | Detection Limit = 0.046 ng/ml |

Calibration Ratio = Normalisation ratio = $\frac{\text{Expected calibrator value}}{\text{Observed calibrator value}}$ The effect of the aging of reagents on detection limits with SPC was also assessed. The antibody conjugate reagents were stored for up to 7 days at 30° C. This resulted in a decrease of enzyme activity and therefore in final OD obtained with these aged reagents. The aging experiments were therefore designed to assess whether the calibrator could normalise lowered signals which when read off the base curve gave the correct result. FIG. 7 demonstrates the results and shows there was little difference between the non-antigen SPC derived sensitivity and standard curve derived values.

Accuracy/Recovery Dilutions

The accuracy of the assay was evaluated by two methods:

1) Various concentrations of purified prolactin was added to a series of pooled patient samples. The results were calculated by standard curve fitting procedure and by single point calibration procedure.

2) Individual patient samples were diluted by 2-fold dilutions using prolactin assay diluent. The results were calculated by standard curve and single point calibration procedures.

Both fresh and aged (5 days at 30° C.) reagents were used. The results are presented for spiked and diluted samples in Tables 3 and 4 respectively.

TABLE 3

Spiking and Recovery Data

| Sample value unspiked Fresh Reagent standard curve | Prolactin Added | % Recovery | | | |
|---|---|---|---|---|---|
| | | Fresh Reagents | | 5 days at 30° C. | |
| | | STD Curve | SPC | STD Curve | SPC |
| 1) 22.5 | a. 177.3 | 91.1 | 93.9 | 101.1 | 125.7 |
| | b. 81.5 | 90.3 | 95.4 | 100.2 | 93.4 |
| | c. 46.9 | 86.1 | 89.7 | 91.5 | 82.5 |
| | d. 24.0 | 90.1 | 92.5 | 116.5 | 86.3 |
| 2) 11.45 | a. 177.3 | 94.7 | 97.7 | 106.7 | 128.8 |
| | b. 81.5 | 90.2 | 94.1 | 101.8 | 94.6 |
| | c. 46.9 | 103.9 | 89.4 | 119.7 | 109.0 |
| | d. 24.0 | 86.6 | 86.1 | 105.3 | 106.2 |
| 3) 9.9 | a. 177.3 | 99.6 | 102.4 | 102.9 | 120.6 |
| | b. 81.5 | 91.8 | 99.1 | 119.6 | 112.8 |
| | c. 46.9 | 91.2 | 92.7 | 110.1 | 101.1 |
| | d. 24.0 | 92.5 | 91.7 | 120.8 | 111.3 |
| 4) 4.41 | a. 177.3 | 99.6 | 102.7 | 112.8 | 138.8 |
| | b. 81.5 | 93.9 | 96.7 | 111.1 | 103.9 |
| | c. 46.9 | 95.3 | 96.0 | 109.9 | 101.8 |
| | d. 24.0 | 104.6 | 101.5 | 115.3 | 112.1 |

| Summary | $\bar{x}$ + SD | | $\bar{x}$ + SD | |
|---|---|---|---|---|
| | STD Curve | SPC | STD Curve | SPC |
| a) | 96.75 ± 4.3 | 99.2 ± 4.2 | 105.8 ± 5.2 | 128.5 ± 7.7 |
| b) | 91.55 ± 1.7 | 96.3 ± 2.1 | 108.2 ± 9 | 101.2 ± 9 |
| c) | 94.13 ± 7.5 | 91.95 ± 3.1 | 107.8 ± 11.8 | 98.6 ± 11.3 |
| d) | 93.45 ± 7.8 | 92.95 ± 6.4 | 114.5 ± 6 | 103.97 ± 12.0 |

TABLE 4

Patient Sample Analytical Dilutions

% mean recovery

| Dilutions | n | Fresh Reagent | | Aged Reagents | |
|---|---|---|---|---|---|
| | | STD Curve | SPC | STD Curve | SPC |
| 1/2 | 10 | 99.5 ± 9.3 | 98.6 ± 7.6 | 98.6 ± 6.8 | 91.3 ± 6.7 |
| 1/4 | 10 | 97.8 ± 8.4 | 94.4 ± 8.5 | 96.7 ± 7.5 | 86.7 ± 7.0 |
| 1/8 | 10 | 97.7 ± 8.4 | 91.7 ± 7.8 | 95.5 ± 8.7 | 83.6 ± 8.6 |
| 1/16 | 10 | 93.0 ± 6.9 | 86.3 ± 5.0 | 89.6 ± 10.2 | 76.02 ± 6.8 |

In Table 5 is presented the results of larger diagnostic dilutions of high patient samples. Such samples read out of the standard curve range and therefore must be diluted to give a measurable value. The % recovery observed by standard curve and single point procedure using both fresh and aged reagents were acceptable.

TABLE 5

Patient Samples Diagnostic Dilutions - Very High Samples diluted to bring them on the standard curve % mean recovery TABLE 5-continued Patient Samples Diagnostic Dilutions - Very High Samples diluted to bring them on the standard curve

| Neat 1/25 100% R. | n | Fresh Reagent | | Aged Reagents | |
|---|---|---|---|---|---|
| | | STD Curve | SPC | STD Curve | SPC |
| 1/50 | 4 | 101.2 ± 4.9 | 91.2 ± 5.09 | 92.6 ± 4.8 | 90.0 ± 9.0 |
| 1/100 | 4 | 108.2 ± 6.2 | 90.0 ± 6.1 | 100 ± 5.0 | 94.8 ± 7.9 |

Patient sample values were calculated by prolactin IEMA standard curve and by single point calibration using fresh and aged reagents. The same samples were also evaluated in the prolactin IRMA.

The following line equations and regression coefficients were obtained:

IEMA fresh reagent standard curve vs IEMA fresh reagent SPC a) IEMA SPC = 0.892 IEMA curve − 1.95 × 10$^{-3}$
R = 0.9979
N = 50
See FIG. 8 b) IEMA aged reagent SPC vs IEMA aged reagent standard curve

IEMA SPC = 0.876 IEMA curve −0.7
R = 0.9981
N = 50
See FIG. 9 c) IEMA fresh reagent standard curve vs IRMA MAIAclone (Serono Diagnostics Ltd)

IEMA = 1.08 IRMA − 0.54
R = 0.9920
N = 50

Single point calibration values according to this study appear to read approximately 10% lower than the standard curve values for fresh and aged reagents, but the results obtained by SPC are nevertheless still acceptable.

Specificity

Human placental lactogen (HPL) and human growth hormone (HGH) cross-reactivity was examined with the single point calibration procedure as shown in Table 6.

TABLE 6

Analyte cross-reactivity in Prolactin IEMA

Apparent HPRL concentration ng/ml

| Analyte Amount Added | Fresh Reagent | | Aged Reagent | |
|---|---|---|---|---|
| | STD Curve | SPC | STD Curve | SPC |
| HPL | | | | |
| 0.09 | <DL | 0 | 0 | 0 |
| 0.19 | <DL | 0 | <DL | 0 |
| 0.39 | 0 | 0 | <DL | 0 |
| 0.78 | 0 | 0 | <DL | 0 |
| 1.5 | 0 | 0 | 0 | 0 |
| 3.25 | 0 | 0 | 0 | 0 |
| 6.15 | 0 | 0 | <DL | 0 |
| 12.75 ng/ml | <DL | 0 | <DL | 0 |
| hGH | | | | |
| 0.5 mIU/ml | <DL | <DL | 0 | 0 |
| 1.0 | 0.12 | 0.11 | 0.13 | 0 |

TABLE 6-continued

Analyte cross-reactivity in Prolactin IEMA

| | Apparent HPRL concentration ng/ml | | | |
|---|---|---|---|---|
| | Fresh Reagent | | Aged Reagent | |
| Analyte Amount Added | STD Curve | SPC | STD Curve | SPC |
| 2.5 | 0.375 | 0.21 | 0.345 | <DL |
| 5.0 | 0.72 | 0.496 | 0.68 | 0.38 |
| 10.0 | 1.475 | 1.1 | 1.4 | 0.925 |

There is no significant difference between the cross-reactivity observed with fresh and aged reagents.

Key to FIGS. 3 to 7

FIG. 3 shows the precision profile where:
  △—△ = freeze-dried antigen calibrator in single point calibration (SPC) as described hereinbefore
  ●—● = manual standard curve precision;
FIG. 4 shows the bias profiles where:
  a = freeze-dried antigen calibrator
  b = non-antigen calibrator
  HPRL = human prolactin
FIGS. 5a and 5b show the titration of sheep anti-mouse FITC (non-antigen calibrator);
FIG. 6 shows the precision profile where:
  ●—● = non-antigen calibrator
  ●—● = manual curve values
FIG. 7 shows the effect of reagent ageing on sensitivity wherein:
  △—△ = non-antigen calibrator
  ●—● = standard curve
  x—x = calibrator normalisation factor (% of Day O value);

We claim:

1. In a method of assay for a ligand in a sample comprising
  (1) incubating in a first solution the sample, sequentially or simultaneously, with a first specific binding partner to the ligand and with a predetermined amount of reagent X, wherein reagent X comprises a second specific binding partner to said ligand, bound directly or indirectly to a detectable label, or a ligand analogue, bound directly or indirectly to a detectable label, thereby forming a complex between said first specific binding partner and reagent X, the amount of reagent X in the complex being a function of the amount of ligand in the sample;
  (ii) removing said first specific binding partner from the solution by binding said first specific binding partner to a first solid phase reagent and separating said first solid phase reagent from the solution; and
  (iii) determining, by means of said detectable label, the amount of reagent X bound to said first solid phase reagent, the improvement comprising normalizing the assay by comparison with a calibration assay, said calibration assay comprising
  (a) incubating in a sample free second solution a predetermined amount of said reagent X with a calibration reagent Y comprising a specific binding partner for said reagent X other than the ligand and which is stable in solution at working concentrations and temperatures, thereby forming a complex between reagent Y and reagent X in a predictable and reliable manner;
  (b) removing said calibration reagent Y from said second solution by binding said calibration reagent Y to a second solid phase reagent and separating said second solid phase reagent from the solution in the same manner as that used to remove the first specific binding partner in step (ii); and
  (c) determining, by means of said detectable label, the amount of reagent X bound to said second solid phase reagent.

2. The method of claim 1 wherein the predetermined amount of reagent X used in the assay and the calibration assay is identical.

3. The method of claim 1 wherein the ligand is an antigen.

4. The method of claim 3 wherein the first specific binding partner to the ligand is a hapten-labelled antibody directed against the ligand and said first solid phase reagent comprises an antibody directed against said hapten.

5. The method of claim 4 wherein said reagent Y comprises a hapten-labelled antibody directed against reagent X, wherein said hapten-label is the same as that used in said first specific binding partner, and said second solid phase reagent is identical to said first solid phase reagent.

6. The method of claim 5 wherein said reagent X is an antibody directed against said ligand.

7. The method of claim 6 wherein the detectable label of reagent X is a radioactive isotope, a fluorophore or an enzyme.

8. The method of claim 7 wherein the ligand is prolactin.

9. In a method of assay for a ligand in a sample comprising
  (i) incubating in a first solution the sample, sequentially or simultaneously, with a hapten-labelled first specific binding partner to the ligand and with a predetermined amount of reagent X, wherein reagent X comprises a second specific binding partner to said ligand, bound directly or indirectly to a detectable label, or a ligand analogue, directly or indirectly to a detectable label, thereby forming a complex between said first specific binding partner and reagent X, the amount of reagent X in the complex being a function of the amount of ligand in the sample;
  (ii) removing said first specific binding partner from the solution by binding said first specific binding partner to a first solid phase reagent and separating said first solid phase reagent from the solution; and
  (iii) determining, by means of said first detectable label, the amount of reagent X bound to said first solid phase reagent, the improvement comprising normalizing the assay by comparison with a calibration assay, said calibration assay comprising
  (a) incubating in a sample free second solution a predetermined amount of calibration reagent Z which is other than the ligand and which comprises said hapten-label bound, directly or indirectly, to said detectable label and which is stable in solution at working concentrations and temperatures with a specific binding partner for said hapten, thereby forming a complex between reagent Z and its specific binding partner in a predictable and reliable manner;
  (b) removing said calibration reagent Z from said second solution by binding said calibration reagent Z to a second solid phase reagent and separating said second solid phase reagent from the solution in the same manner as that used to remove the first specific binding partner from solution in step (ii); and (c) determining, by means of said detectable label, the amount of detectable label bound to said second solid phase reagent.

10. The method of claim 9 wherein calibration reagent Z is reagent X with a hapten-label.

11. The method of claim 10 wherein the predetermined amount of reagent X used in the assay is the same as the predetermined amount of reagent Z used in the calibration assay.

12. The method of claim 10 wherein the ligand is an antigen.

13. The method of claim 12 wherein the first specific binding partner to the ligand is a hapten-labelled antibody directed against the ligand.

14. The method of claim 13 wherein said reagent X is an antibody directed against said ligand.

15. The method of claim 14 wherein the detectable label is a radioactive isotope, a fluorophore or an enzyme.

16. The method of claim 15 wherein the ligand is prolactin.

17. The method of claim 10 wherein said first and second solid phase reagents each comprise an antibody directed against said hapten-label.

18. The method of claim 17 wherein said first and second solid phase reagents are identical.

19. A kit for carrying out a method of assay as claimed in claim 11, said kit comprising a reagent X, a first specific binding partner to the ligand and a calibration reagent Y, wherein reagent X comprises a second specific binding partner to the ligand to be assayed, bound directly or indirectly to a detectable label, or a ligand analog bound directly or indirectly to a detectable label, and reagent Y comprises a specific binding partner for said reagent X other than the ligand.

20. A kit for carrying out a method of assay as claimed in claim 9, said kit comprising a reagent X, a hapten-labelled first specific binding partner to the ligand and a calibration reagent Z, wherein reagent X comprises a second specific binding partner to the ligand to be assayed, bound directly or indirectly to a detectable label, or a ligand analog, bound directly or indirectly to a detectable label, and reagent Z comprises said hapten-label bound, directly or indirectly, to said detectable label and which is stable in solution at working concentrations and temperatures.

* * * * *